(12) United States Patent
Lees

(10) Patent No.: US 6,315,260 B1
(45) Date of Patent: Nov. 13, 2001

(54) THREE-DIMENSIONAL SWINGER CLAMP FOR LOCKING VERTICAL SUPPORT IN PLACE

(75) Inventor: John Lees, Richmond, VA (US)

(73) Assignee: Automated Medical Products, Corp., Sewaren, NJ (US)

( * ) Notice: Subject to any disclaimer, the term of this patent is extended or adjusted under 35 U.S.C. 154(b) by 0 days.

(21) Appl. No.: 09/513,830

(22) Filed: Feb. 25, 2000

Related U.S. Application Data
(60) Provisional application No. 60/124,927, filed on Mar. 18, 1999.

(51) Int. Cl.$^7$ .................................................... E04G 3/00
(52) U.S. Cl. ................................... 248/286.1; 248/287.1; 248/296.1; 403/14; 600/201
(58) Field of Search ............................. 248/286.1, 287.1, 248/284.1, 296.1, 295.11, 292.12, 298.1; 600/201; 602/32, 33, 35, 36; 5/648; 403/13, 14, 260, 257, 374.2, 374.4

(56) References Cited

U.S. PATENT DOCUMENTS

| | | | |
|---|---|---|---|
| 2,622,831 | * 12/1952 | Fullwood . | |
| 3,046,072 | * 7/1962 | Douglass, Jr. et al. . | |
| 3,339,913 | 9/1967 | Anderson . | |
| 4,143,652 | 3/1979 | Meier et al. . | |
| 4,461,284 | 7/1984 | Fackler . | |
| 4,491,435 | 1/1985 | Meier . | |
| 4,547,092 | * 10/1985 | Vetter et al. ................... | 248/296.1 X |
| 4,718,151 | 1/1988 | LeVahn et al. . | |
| 4,796,846 | 1/1989 | Meier et al. . | |
| 4,875,651 | * 10/1989 | Wergin et al. ..................... | 248/286.1 |
| 4,945,897 | 8/1990 | Greenstein et al. . | |
| 5,025,780 | 6/1991 | Farley . | |
| 5,135,210 | * 8/1992 | Michelson . | |
| 5,162,039 | 11/1992 | Dahners . | |
| 5,224,680 | 7/1993 | Greenstein et al. . | |
| 5,365,921 | 11/1994 | Bookwalter et al. . | |
| 5,441,042 | 8/1995 | Putman . | |
| 5,529,571 | 6/1996 | Daniel . | |
| 5,538,215 | 7/1996 | Hosey . | |
| 5,662,300 | 9/1997 | Michelson . | |
| 5,755,412 | 5/1998 | Guibert et al. . | |
| 5,876,332 | 3/1999 | Looney . | |
| 5,931,777 | 8/1999 | Sava . | |

FOREIGN PATENT DOCUMENTS

WO 97/40752    11/1997  (WO) .

OTHER PUBLICATIONS

A.C. Stieber, Hepatic Transplantation With the Aid of the Iron Intern Retractor, The American Journal of Surgery, vol. 160, pp. 300–301, Sep. 1990.

R.J. Greenstein, Mechanical Retraction in Obesity and Esophagogastric Surgery, vol. 1, pp. 431–433, 1991.

* cited by examiner

Primary Examiner—Ramon O. Ramirez
Assistant Examiner—Korie Chan
(74) Attorney, Agent, or Firm—Blank Rome Comisky & McCauley LLP

(57) ABSTRACT

A swinger clamp is clamped onto a horizontal guide rail and supports a vertical bar to hold various devices during surgical procedures. The clamp has a damper jaw that abuts a rim. To prevent the rim from drifting in its rotational position relative to the clamping jaw, a groove is formed in the rim to engage with the damper jaw.

4 Claims, 2 Drawing Sheets

THREE-DIMENSIONAL SWINGER CLAMP FOR LOCKING VERTICAL SUPPORT IN PLACE

REFERENCE TO RELATED APPLICATION

This application claims the benefit of U.S. Provisional Application No. 60/124,927, filed Mar. 18, 1999, which is hereby incorporated by reference in its entirety into the present disclosure.

FIELD OF THE INVENTION

The present invention is directed to a 3D (three-dimensional) swinger clamp for a rib grip used in abdominal surgery and is further directed to such a swinger clamp that has a groove for locking a jaw of the swinger clamp in place.

DESCRIPTION OF RELATED ART

The swinger clamp according to the present invention is an improvement on the swinger clamp of U.S. Pat. No. 4,796,846, issued to Meier et al on Jan. 10, 1989, and hereinafter known as the '846 patent, whose disclosure is hereby incorporated by reference in its entirety into the present disclosure.

Swinger clamps are used in the surgical arts to support various devices used during surgery. A swinger clamp is clamped onto a horizontal guide rail, and a vertical bar is inserted into the swinger clamp. The vertical bar can support, either directly or via a horizontal bar attached to the top of the vertical bar, any of numerous devices. For example, during a liver transplant, it is often necessary to hold the rib cage up and the stomach out of the way; retaining devices can be attached to the above-mentioned horizontal bar to perform those functions. A well known example of that technology is the Iron Intern® sold by the assignee of both the above-cited '846 patent and the present application However, the swinger clamp of the '846 patent presents a problem that will be explained with reference to FIGS. 1 and 1a of that patent, which are reproduced herein with the same figure numbers. When the clamp is clamped onto the guide rail, the rim 43 may drift in its rotational position relative to the clamping jaw 18. Thus, anything attached to the swinger clamp will drift out of its correct position

SUMMARY OF THE INVENTION

In light of the foregoing, it will be readily apparent that a need exists in the art for a swinger clamp that provides increased stability for the vertical bar and resists slipping. Therefore, a primary object of the invention is to provide a swinger clamp that locks the vertical bar into position.

It is a further object of the invention to provide a swinger clamp that locks the vertical bar into position via a simple, rugged mechanical articulation.

It is a still further object of the invention to provide a swinger clamp that provides extra stability when the vertical bar is used in extreme circumstances, such as obesity procedures and liver retraction for transplant.

It is a yet further object of the invention to provide a swinger clamp that can, at the option of the user, meet the above objects or be used like the swinger clamp of the above-referenced U.S. patent.

To achieve these and other objects, the present invention is directed to a swinger clamp like that of the above-referenced U.S. patent, except that a groove is provided in the rim. The clamping jaw engages and is locked in the groove to provide stability to the vertical bar by mechanical articulation.

BRIEF DESCRIPTION OF THE DRAWINGS

A preferred embodiment of the present invention will now be set forth in detail with reference to the figures, in which.

DETAILED DESCRIPTION OF THE PREFERRED EMBODIMENT

Figure 1:
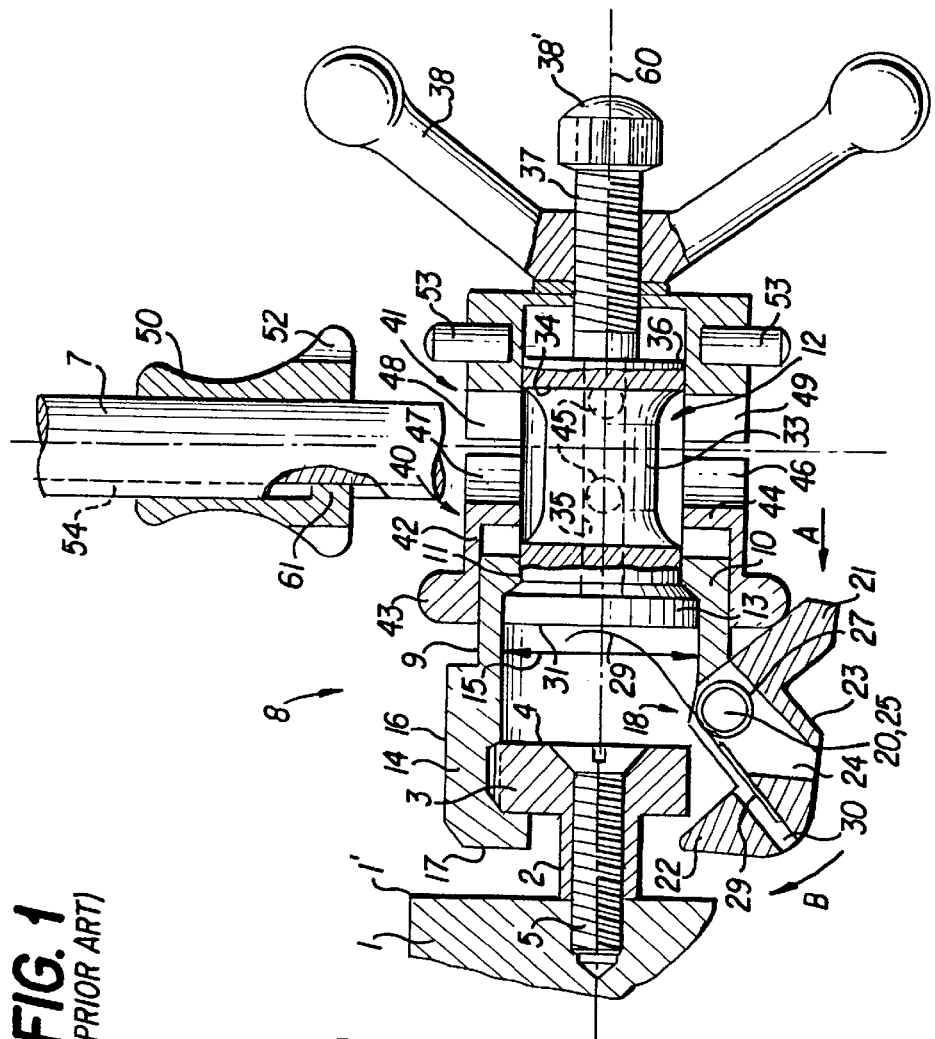
FIG. 1 shows a perspective view of the swinger clamp according to the '846 patent.
Figure 1A:
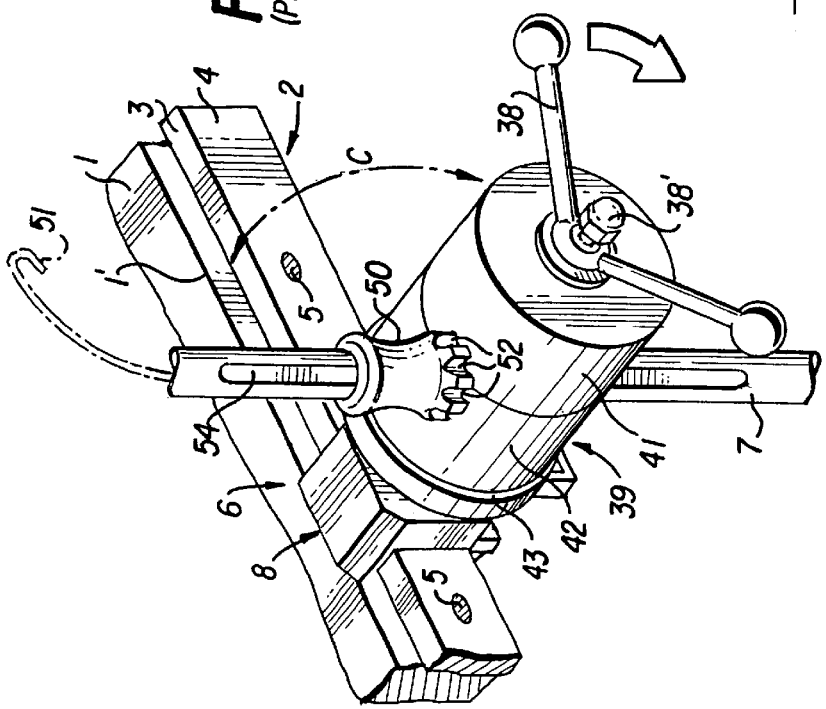
FIG. 1a shows a cross-sectional view of the swinger clamp of FIG. 1.
Figure 2:
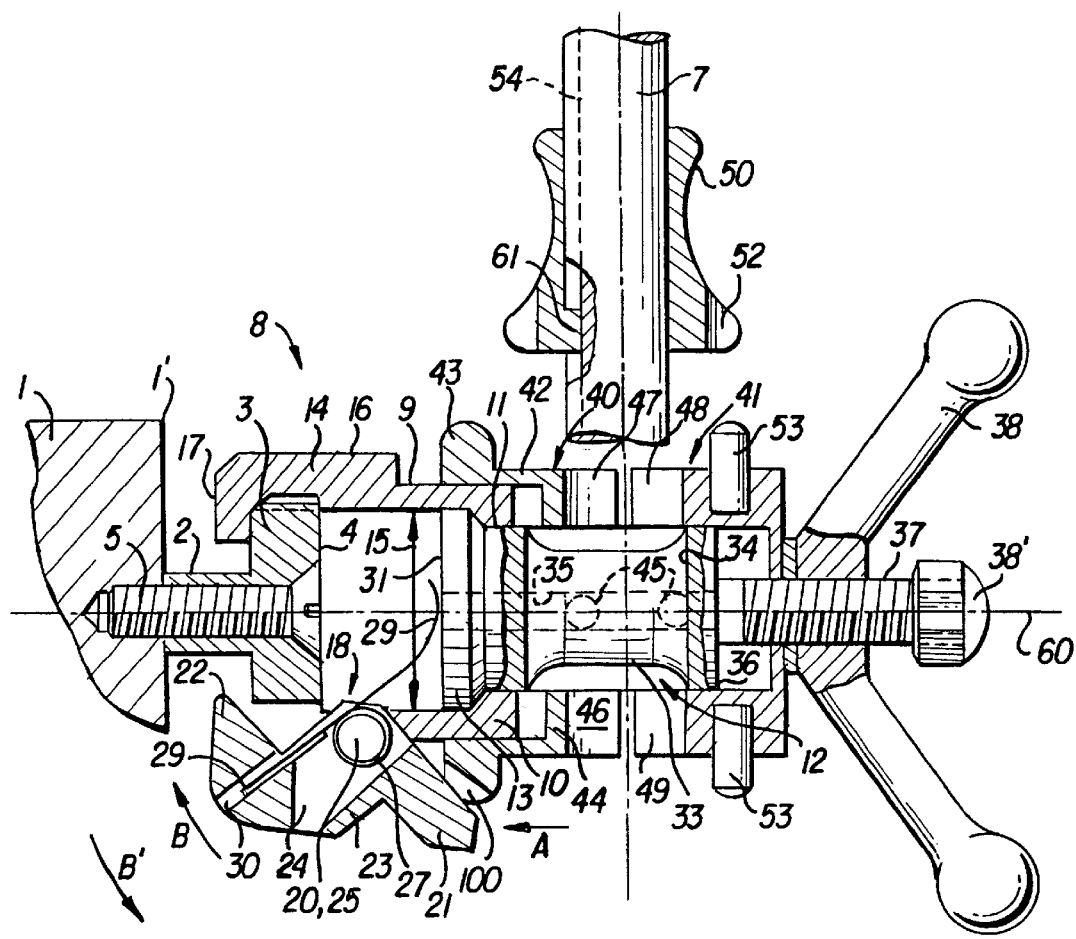
FIG. 2 shows a cross-sectional view of a swinger clamp according to a preferred embodiment of the present invention.
Figure 3:
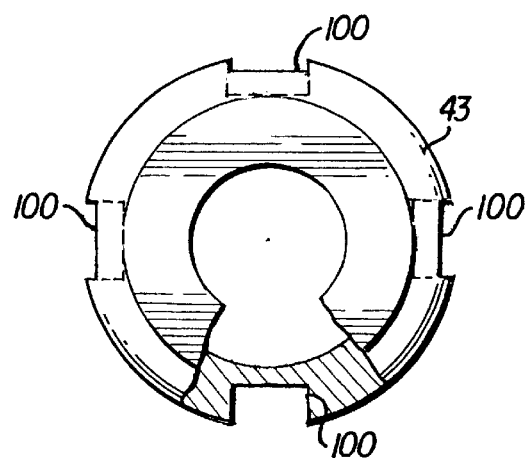
FIG. 3 shows a head-on view of the rim and groove of the swinger clamp of FIG. 2.

FIG. 2 shows a cross-sectional view of the swinger clamp according to the preferred embodiment. The swinger clamp of FIG. 2 differs from that of FIGS. 1 and 1a in that a groove 100 is formed in the rim 43. The groove 100 is sized so that it can accommodate the clamping jaw 18 with a minimum of play when the spring 26 urges the clamping jaw 18 all the way in the counterclockwise direction indicated by the arrow B'. FIG. 3 shows a head-on view of the rim 43 with the groove 100 formed therein. Thus, the clamping jaw 18 and the rim 43 are locked into their relative rotational position. Otherwise, the swinger clamp according to the preferred embodiment is constructed and used like that of the '846 patent, so that reference is made to that patent for the details of construction and use.

While a preferred embodiment has been set forth above, those skilled in the art who have reviewed the present disclosure will readily appreciate that other embodiments can be realized within the scope of the invention. For example, multiple grooves 100 can be provided around the rim 43 to allow multiple relative rotational positions between the clamping jaw 18 and the rim 43, as shown in FIG. 3 with dotted lines. Also, the invention can be applied to swinger clamps other than the one specifically disclosed. Moreover, the invention is not strictly limited to surgical applications. Therefore, the present invention should be construed as limited only by the appended claims.

What is claimed is:

1. A swinger clamp for supporting a bar in a desired position relative to a guide rail, the swinger clamp comprising:

a holder block for being clamped onto the guide rail, the holder block comprising a clamping jaw that is movable for releasably clamping the holder block onto the guide rail; and a gripping mechanism for gripping the bar, the gripping mechanism being attached to the holder block such that when the holder block is clamped onto the guide rail and the gripping mechanism grips the bar, the gripping mechanism supports the bar in the desired position relative to the guide rail;

wherein:

the gripping mechanism is rotatable relative to the holder block and has a rim that abuts the clamping jaw; and the rim has a groove for receiving the clamping jaw such that when the holder block is clamped onto the guide rail and the gripping mechanism grips the bar, rotational movement of the gripping mechanism relative to the holder block is prevented by an engagement of the clamping jaw with the groove.

2. The swinger clamp of claim 1, wherein the rim has a plurality of said grooves to permit the gripping mechanism to be locked into any one of a plurality of rotational orientations relative to the holder block.

3. The swinger clamp of claim 1, wherein the clamping jaw comprises a spring for urging the clamping jaw into a position in which the holder block is clamped onto the guide rail.

4. The swinger clamp of claim 1, wherein the holder block and the gripping mechanism are formed as separate pieces that are engaged with each other.

* * * * *